(12) United States Patent
Noack

(10) Patent No.: US 9,526,405 B2
(45) Date of Patent: Dec. 27, 2016

(54) STEREOENDOSCOPE

(75) Inventor: Andreas Noack, Dragen (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 427 days.

(21) Appl. No.: 13/821,984

(22) PCT Filed: Sep. 12, 2011

(86) PCT No.: PCT/EP2011/004573
§ 371 (c)(1),
(2), (4) Date: Mar. 10, 2013

(87) PCT Pub. No.: WO2012/041446
PCT Pub. Date: Apr. 5, 2012

(65) Prior Publication Data
US 2013/0162776 A1    Jun. 27, 2013

(30) Foreign Application Priority Data
Oct. 1, 2010 (DE) .......... 10 2010 041 857

(51) Int. Cl.
*A61B 1/04* (2006.01)
*A61B 1/00* (2006.01)
*H04N 13/02* (2006.01)
*A61B 1/05* (2006.01)

(52) U.S. Cl.
CPC ......... *A61B 1/00193* (2013.01); *A61B 1/0008* (2013.01); *A61B 1/00179* (2013.01); *A61B 1/00183* (2013.01); *A61B 1/05* (2013.01); *H04N 13/02* (2013.01)

(58) Field of Classification Search
CPC ............ A61B 1/00002; A61B 1/00013; A61B 1/0008; A61B 1/005; A61B 1/00193; A61B 1/00179; A61B 1/05

USPC .......................................................... 348/45
See application file for complete search history.

(56) References Cited

U.S. PATENT DOCUMENTS

| 5,321,447 A | 6/1994 | Sander et al. |
| 5,588,948 A | 12/1996 | Takahashi et al. |
| 5,612,816 A | 3/1997 | Strahle et al. |
| 5,689,365 A * | 11/1997 | Takahashi ..................... 359/362 |
| 5,702,350 A | 12/1997 | Vry et al. |
| 5,720,706 A | 2/1998 | Takahashi et al. |

(Continued)

FOREIGN PATENT DOCUMENTS

| DE | 295 04 623 U1 | 10/1995 |
| DE | 10 2010 041 847 A1 | 4/2012 |

(Continued)

OTHER PUBLICATIONS

English Language Abstract only of WO 12041445A.
International Search Report dated Dec. 1, 2011 issued in corresponding International Application No. PCT/EP2011/004573.

*Primary Examiner* — Farzana Hossain
(74) *Attorney, Agent, or Firm* — Scully, Scott, Murphy & Presser, P.C.

(57) ABSTRACT

A stereo endoscope having an elongated shaft and a sensor unit comprising two flat image sensors that are symmetrically arranged about a central rotational axis of the shaft. With such stereo endoscope, a lateral direction of view of the stereo endoscope which deviates from a central 0° direction of view can be variably adjusted and/or changed independent of an orientation of the image sensors relative to each other.

10 Claims, 3 Drawing Sheets

(56) References Cited

U.S. PATENT DOCUMENTS

| | | | |
|---|---|---|---|
| 5,743,846 A | 4/1998 | Takahashi et al. | |
| 5,743,847 A | 4/1998 | Nakamura et al. | |
| 5,825,534 A | 10/1998 | Strähle | |
| 6,306,082 B1 | 10/2001 | Takahashi et al. | |
| 6,450,950 B2* | 9/2002 | Irion | 600/170 |
| 6,976,956 B2 | 12/2005 | Takahashi et al. | |
| 2006/0126176 A1* | 6/2006 | Nogami | A61B 1/0005 359/464 |
| 2009/0076329 A1 | 3/2009 | Su et al. | |
| 2010/0137685 A1* | 6/2010 | Rovegno | 600/109 |
| 2011/0228049 A1* | 9/2011 | Kazakevich | A61B 1/0005 348/45 |
| 2011/0288560 A1* | 11/2011 | Shohat et al. | 606/130 |

FOREIGN PATENT DOCUMENTS

| | | |
|---|---|---|
| EP | 1 681 013 A1 | 7/2006 |
| JP | 6-59199 A | 3/1994 |
| JP | 8-76030 A | 3/1996 |
| JP | 8-82766 A | 3/1996 |
| JP | 8-194170 A | 7/1996 |
| JP | 10-192233 A | 7/1998 |
| JP | 2007-151862 A | 6/2007 |

\* cited by examiner

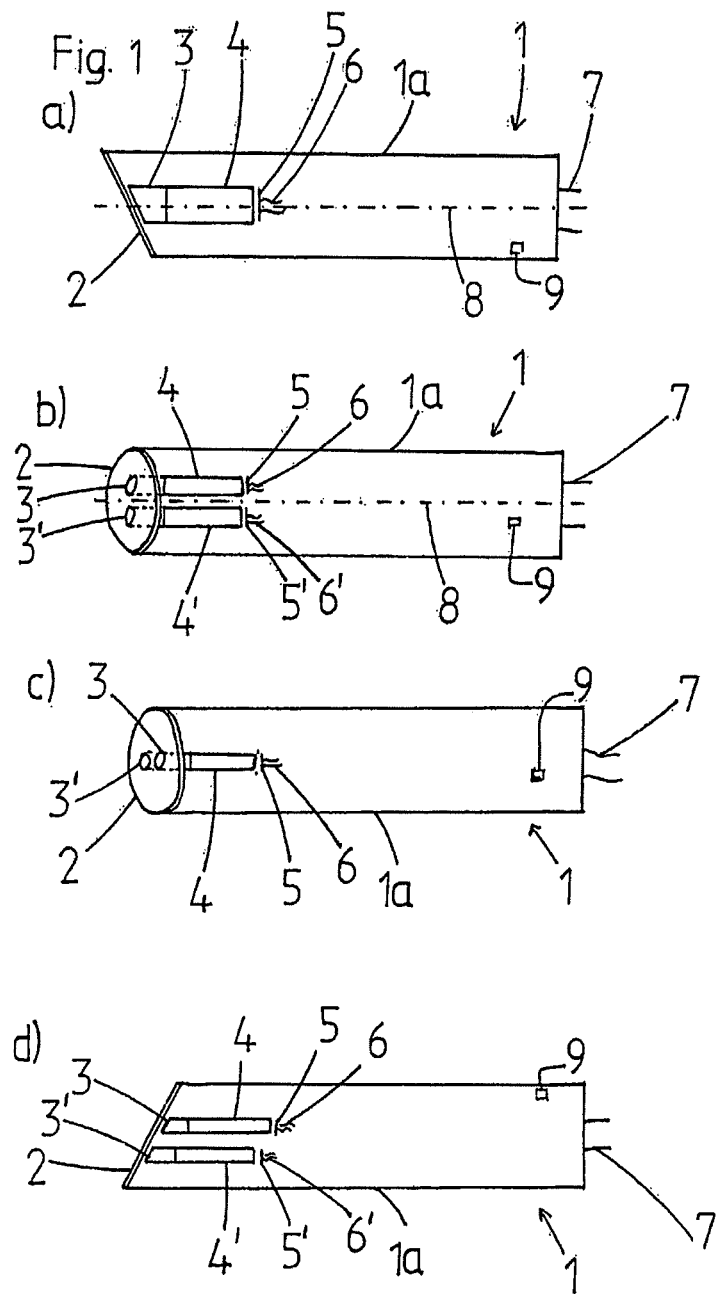

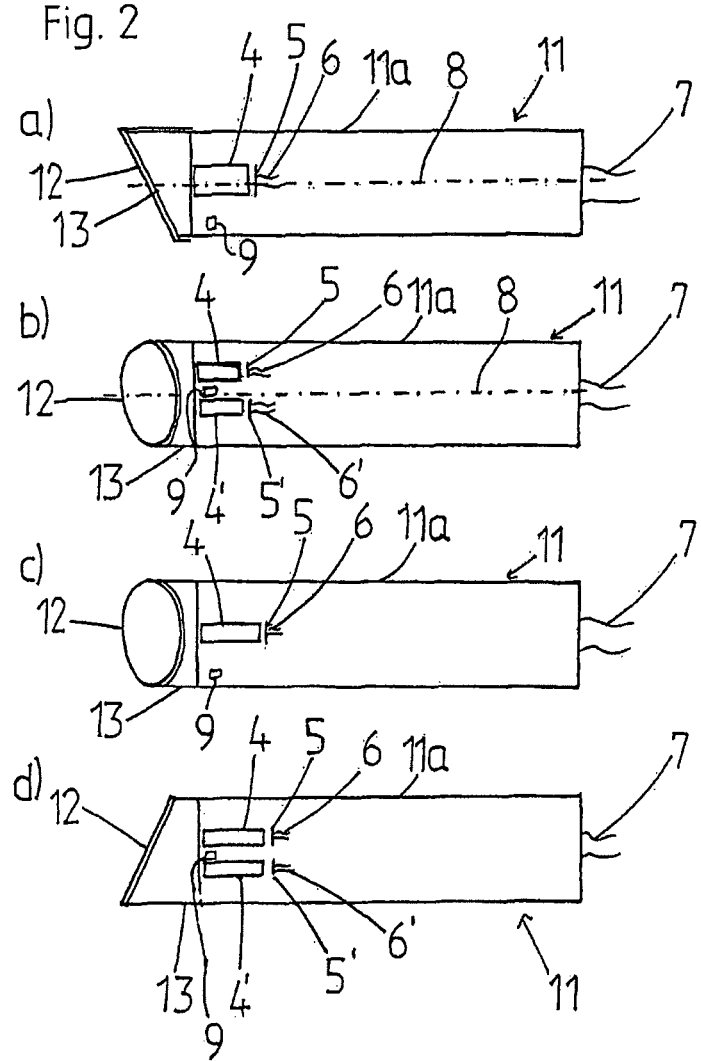

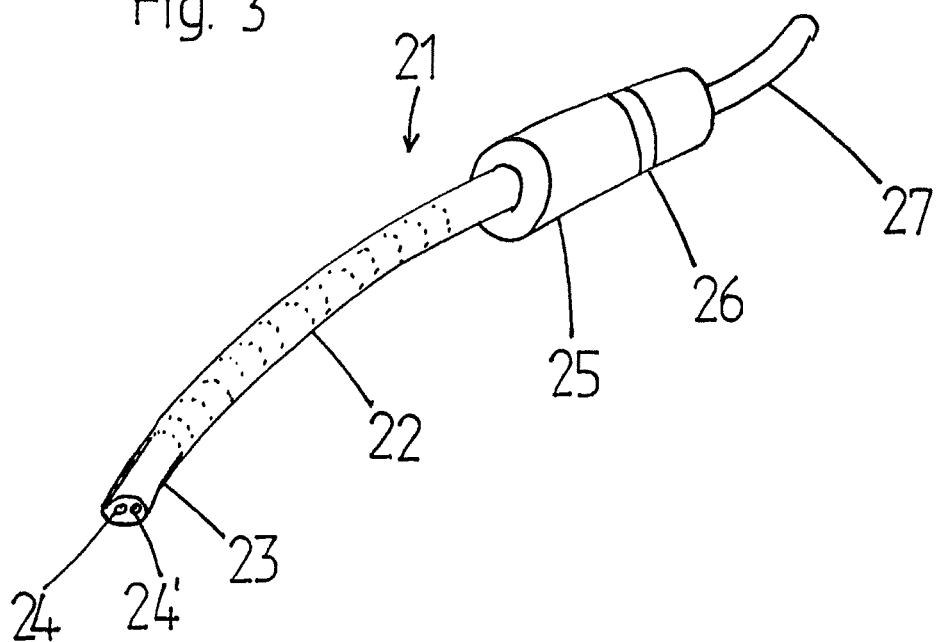
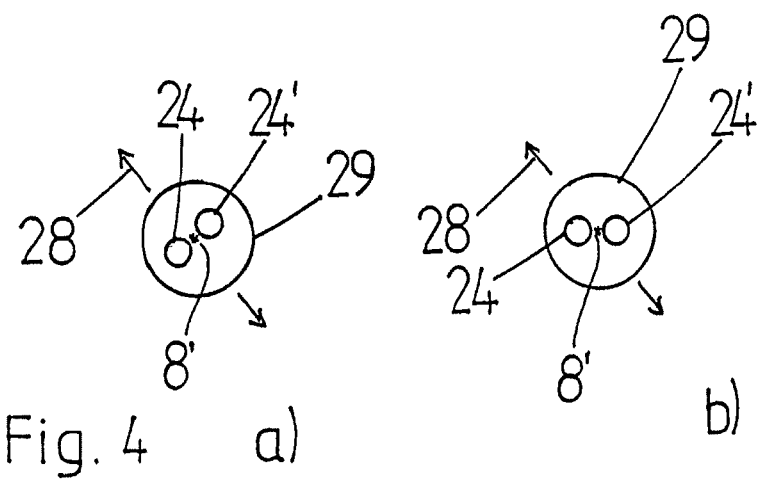

STEREOENDOSCOPE

CROSS-REFERENCE TO RELATED APPLICATIONS

This application claims priority to PCT Application EP2011/004373 filed on Sep. 12, 2011, which claims priority to Application No. DE 10 2010 041 857.9 filed on Oct. 1, 2010, the contents of each of which are incorporated herein by reference.

DESCRIPTION

The invention relates to a stereo endoscope having an elongated shaft and a sensor unit comprising two flat image sensors which are arranged symmetrically about a central rotational axis of the shaft.

Minimally invasive endoscopic surgery of the human or animal body is performed using endoscopes with a long or respectively elongated shaft that is introduced into the interior of or respectively a cavity in the body through a body opening existing or created for this purpose before surgery. Since the operative field in the body cavity cannot be viewed directly from the outside, known endoscopes enable a view of the body cavity to be treated. For this purpose, conventional endoscopes have an optical system with one or more lenses on the distal tip of the endoscope shaft that direct light from the body cavity into the endoscope. The endoscope shaft can have an arrangement of lenses such as rod lenses by means of which light is guided out of the body cavity to the proximal end of the endoscope, that is, to the end that is held and used by the operator or surgeon.

In the proximal region of the endoscope, for example on a handle, there is an eyepiece with an ocular, that is, an optical system, from which exits the light entering the distal tip of the endoscope. Such an ocular can be used for direct observation with a naked eye brought up to the eyepiece.

An alternative possibility is to connect a camera head to the eyepiece on the proximal end of the endoscope which camera head has its own optical system that guides the light exiting the ocular to a flat optical matrix sensor such as a CCD chip or a CMOS chip. The image recorded by the optical matrix sensor can for example be displayed on a monitor and saved, if necessary, so that it can be retrieved later, if necessary, and displayed.

In video endoscopy systems, it is alternatively known to insert an image sensor in the distal tip of the shaft of the endoscope next to an optical system, and the image or respectively video signals are electronically transmitted.

Endoscopes and endoscopic instruments are used in the surgery of human or animal bodies within narrow spaces. Frequently, sections of tissue which are essential to life or functioning are directly adjacent to the parts of tissue to be operated on. Consequently, it is fundamentally important for the performing surgeon to have well-functioning hand-eye coordination and orientation when using an endoscope.

Most current systems offer a flat, two-dimensional impression of the operative field so that potential training for hand-eye coordination is restricted. The perception and estimation of distances and relative spatial relationships is difficult in comparison to the direct viewing of an operative field.

A three-dimensional representation of the operative field promises an improvement in this regard given the achievable plasticity of the reproduced image. Stereo endoscopic systems are already known. The known approach of generating a three-dimensional view of the operative field by means of a single endoscope is substantially based on the implementation of two image channels in the endoscope. Since the two image channels at the tip of the endoscope are slightly apart from each other due to the narrow design of endoscopes, it is possible to depict a three-dimensional visual range of a few millimeters to centimeters in front of the tip of the endoscope. This is sufficient in most applications.

In many cases, endoscopes have a rigid shaft. In order to cover the largest possible viewing angle within the interior of the body, such endoscopes are equipped with a side view. For this purpose, they have a mirror, prism or other optical deflective element that directs the viewing angle to the side by 30°, 45°, 70° or a desired different angle. For example, with a side viewing angle of 45°, the effective field of vision includes both the 0° direction along the extension of the shaft as well as an orthogonal 90° angle. In order to see the largest possible spatial angle, such an endoscope is rotated about its longitudinal axis.

In contrast to photography where the line of the horizon between the sky and earth is normally depicted horizontally, for example in pictures of landscapes, there are no pictorial references in the recorded image in endoscopy that could provide the surgeon with information on whether the displayed image has the same orientation with reference to his own orientation in space or is, for example, upside down. From the image, the surgeon therefore cannot be sure of the horizon position of the image. If the horizon position in the image, which is determined by the orientation of the image sensors within space, deviates from the position of the surgeon, it makes it difficult for the surgeon to orient himself and use the endoscope. Directed movements of the endoscope cause the image to shift in the wrong direction. The use of the endoscope is disorienting in a manner similar to a cursor on a computer screen being influenced by the movement of a computer mouse which is, for example, held twisted at a 90° angle or another angle.

In the case of monoscopic endoscopes, a camera head with an image sensor is attached to the endoscope eyepiece by means of a coupling that allows the endoscope to be rotated relative to the camera head in order to retain the horizon position for the surgeon. If such rotational decoupling is not possible, the surgeon quickly becomes disoriented due to the rotation of the image together with the rotation of the direction of view of the endoscope.

Such rotational decoupling is not used with known stereo video endoscopy systems since separating the lens groups in the endoscope shaft forming the optical image channels would cause the lens groups of the two image channels of the endoscope shaft to move away from the corresponding lens groups and image sensors in the camera head when the shaft is rotated. By rotating 90°, any overlap would disappear and no image could be seen.

Consequently, the image sensors are not rotatably decoupled from the optical image channels or respectively lens groups in known stereo endoscopy systems.

The horizon position of the image is lost when the endoscope is rotated on its longitudinal axis. A solution to this problem is described in the German patent application No. 10 2010 041 847.1 by the applicant entitled "Sensor unit for a stereo endoscope and stereo endoscopy system" with the same priority, to which reference is expressly made.

In addition to the loss of the horizon position of the image itself, there is an additional problem which is due to the function of stereo endoscopy itself. This function is based on the principle that two image channels are arranged offset by a certain distance along a baseline analogous to the eyes of the viewer. The baseline typically runs horizontally so that one image channel views from the right and the other from the left. The images of both channels are presented by a suitable viewing system only to the right or respectively left eye, and the images are processed in the brain of the viewer into three-dimensional perception.

When the endoscope is rotated, the position of the baseline rotates independent of the alignment of the image sensor. Even though the individual images of both channels can retain the horizon position by correspondingly rotating the image sensors on their midpoint, one channel looks down and the other looks up, for example, when the endoscope is rotated 90°. However, the brain of the viewer of the image does not receive any information on the actual position of the baseline; furthermore, this information could not be processed since the corresponding situation cannot occur physiologically.

By rotating the endoscope, the three-dimensional impression of the image is lost, and in a worst case, it can cause the perception of double images, headaches and dizziness which constitutes undesirable stress on the physician during endoscopic surgery.

The object of the present invention therefore is to provide a stereo endoscope and stereo endoscopy system that allows an operator or a surgeon a three-dimensional depiction of the operative field with a stable horizon position during minimally invasive surgery, even when the direction of view of the endoscope changes.

This object is achieved by a stereo endoscope having an elongated shaft and a sensor unit comprising two flat image sensors which are arranged symmetrically about a central rotational axis of the shaft, and which is further developed in that the lateral direction of view of the stereo endoscope which deviates from a central 0° direction of view is variably adjustable and/or changeable independent of the orientation of the image sensors relative to each other.

In particular, the position of the baseline is meant by "the orientation of the image sensors relative to each other".

Within the context of the invention, the endoscope is generally a sideways-looking endoscope with a direction of view that is changed by rotating about the longitudinal axis of the endoscope, or an endoscope with a flexible shaft that can assume the 0° direction of view aligned in the longitudinal direction of the endoscope, and can assume lateral directions of view deviating therefrom.

Since according to the invention the orientation of the image sensors relative to each other and the lateral direction of view of the stereo endoscope are variably adjustable and/or changeable independent of each other, the adjustment of the line of site is decoupled from the orientation of the image sensors and hence from horizon positions. For the first time, it is therefore possible for a surgeon or operator to select any direction of view that can be depicted by the endoscope without losing the stereoscopic, that is plastic, impression of the operative field and the horizon position of the depicted image. Orientation within the operative field is thereby retained.

The sensor unit is advantageously arranged on a distal tip of the shaft, or in a proximally arranged camera head. In both cases, it is possible to decouple the selected direction of view from the orientation of the image sensors relative to each other.

In an advantageous embodiment of the stereo endoscope according to the invention, the elongated shaft is designed as a rigid shaft the distal end of which has a viewing window which is inclined relative to the longitudinal axis of the shaft and is connected within the shaft to one or two optical deflective elements, especially prisms or reflecting prisms, wherein at least one distal section of the shaft with the viewing window, and the optical deflective element(s), rotate about axes that are aligned parallel to the longitudinal axis of the shaft to adjust or change the lateral direction of view. The sensor unit with the image sensors is preferably also arranged on the tip of the rigid shaft. Alternatively, two rod lens systems are provided parallel to each other, or a common rod lens system forming both channels is provided in the shaft, whereas the sensor unit is arranged in a camera head. This embodiment according to the invention describes an endoscope that has a rigid shaft and a lateral viewing angle which in particular is permanently set. The direction of view is changed by rotating the distal deflective element of the endoscope about the longitudinal axis of the shaft.

Prisms, reflecting prisms and mirrors serve as the optical deflective elements. It is also possible to use movable mirrors that enable a variably adjustable, lateral viewing angle. In such a case of mirrored incident light, it is advantageously provided that the images are reflected again when reproducing the image, in particular about a central, vertical midline of the individual images.

When the corresponding stereo endoscope is rotated about its longitudinal axis, the inclined or respectively sloped viewing window is also rotated so that its direction of inclination also changes. The optical deflective elements rotate in the same direction, in particular when they are prisms with a front surface that is also inclined. If they have an inclined front surface, the viewing window and the front surface of the deflective element remain preferably parallel during rotation.

In a preferred further development, each image sensor is assigned its own optical deflective element, wherein the optical deflective element assigned to an image sensor is rotatable relative to the image sensor about a rotational axis that runs in particular through the midpoint of the image sensor. The combinations of the deflective element and image sensor are, in this case, designed in pairs and execute equivalent movements. The respective axial distance between the image sensor and the deflective element and any lenses or optical systems arranged therebetween does not change during rotation.

When the shaft rotates about its longitudinal axis, preferably only the optical deflective elements rotate synchronously about their respective own central axes, whereas the image sensors do not rotate. The optical deflective elements also do not rotate relative to the image sensors about the central longitudinal axis of the shaft. In this case, no more light from the optical deflective elements would reach their assigned image sensors.

Since the axial position of the viewing window changes relative to the two nonrotating or independently rotating image sensors when the shaft rotates and the inclined viewing window associatedly rotates about the central longitudinal axis of the shaft when changing the direction of view, it is preferably provided that each image sensor is movable along the axial direction of the shaft together with the optical deflective element assigned to the image sensor, in particular including the lenses arranged therebetween, wherein in particular the two image sensors are axially movable in an opposite direction to each other. This compensates the axial component of the rotation of the inclined viewing window.

When the inclined viewing window is rotated, the image sensors and optical deflective elements also relatedly shift axially. This is preferably designed so that the axial movement of the image sensors and the optical deflective elements assigned to them are coupled to the rotary movement of the shaft for changing the direction of view such that the distances between the optical deflective elements and the viewing window remain the same.

As a consequence of this axial shift, the absolute distances between centers of the image sensors change during a rotation. To an individually limited extent, this can be compensated by the human perceptual system without losing the three-dimensional perception. In order to compensate for this variation in the distance between the two image sensors, a radial distance between the image sensors can be changed with the optical deflective elements assigned to them in each case in an advantageous further development, wherein in particular a change in the optical distance is coupled to the axial movement of the image sensors such that the distance of the image sensors perpendicular to the direction of view remains constant.

In another advantageous embodiment of the stereo endoscope according to the invention it is provided that an individual optical deflective element is provided that, in particular, is connected to the viewing window, or comprises the viewing window, wherein the distal end of the shaft together with the optical deflective element can be rotated relative to the sensor unit in order to adjust or change the direction of view of the stereo endoscope, wherein the sensor unit and the image sensors retain their orientation and radial and axial position independent of the rotation of the optical deflective element. In this case, instead of two optical deflective elements, there is only one large optical deflective element, i.e., a mirror, prism or a reflecting prism provided that supplies both image sensors with incident light. In this case, it is unnecessary for the image sensors and/or other components to be axially shiftable. However, a certain amount of axial shiftability can be provided in this case as well and, if applicable, radial shiftability of the image sensors relative to each other in order to compensate for differences in the sections of the path of light directed to the image sensors.

The radial and/or axial shiftability of the image sensors and the optical deflective elements as well as the optical systems or lenses which may be arranged therebetween can be realized either mechanically, for example by means of gear mechanisms, or by electronic actuators such as piezoelectric elements, ultrasonic motors or the like, which are controlled by a control apparatus in the stereo endoscope, or in a stereo endoscopy system.

In another advantageous embodiment of the endoscope according to the invention, the shaft is designed as a flexible shaft, and the sensor unit—that in particular looks directly forward—is arranged in the distal tip, wherein the shaft is designed to adjust or change a lateral direction of view deviating from a central 0° direction of view in at least one plane in a controllable and flexible manner. Corresponding endoscopes are known that can assume a 0° direction of view as well as a lateral direction of view by bending the flexible shaft. An example of this is disclosed in EP 1 681 013 A1. With such an endoscope, the distal tip of the endoscope can be variably controlled in different directions of view in one or more swivel planes.

Use is particularly easy when the shaft is designed to be controllable and flexible in precisely one plane, wherein an azimuth angle can be adjusted by rotating the shaft. This yields particularly robust and easily controllable endoscope guidance. Since the orientation of the image sensors relative each other can be uncoupled from the plane in which the shaft is controlled, the horizon position is retained even after the stereo endoscope is rotated about the longitudinal axis of the shaft. When the shaft is flexible, rotation about the longitudinal axis means rotation about the longitudinal axis of, for example, a handle used by the surgeon to operate the endoscope.

In all cases it is preferably provided that the sensor unit is rotatable relative to the shaft as a whole, wherein a rotation of the shaft to adjust or change the direction of view of the stereo endoscope can be compensated by rotating the sensor unit in the shaft in the opposite direction. A "sensor unit" is to be understood as the functional unit of the image sensors and, if applicable, the associated optical systems and optical deflective elements that can also comprise the viewing window when there is a single optical deflective element. This can be a block or assembly, however, in the context of the invention, a sensor unit can also be understood in that individual components of the sensor unit are driven or controlled so that they move synchronized and/or in the same direction. In the context of the invention, the term "sensor unit" is therefore to be understood as a functional unit with or without a structural unit.

In an advantageous further development it is provided that each image sensor is rotatable about a rotational axis that runs through the center of the image sensor and runs parallel to the longitudinal axis of the shaft. This embodiment is described in German patent application No. 10 2010 041 847.1 entitled "Sensor unit for a stereo endoscope and a stereo endoscopy system" by the applicant and has the same priority as the present application, and its disclosed content is fully incorporated by reference in the present application. In addition it is preferably provided that the image sensors can be rotated relative to each other about the longitudinal axis of the shaft.

This further development enables the individual components of the sensor unit to be independently designed. Both the rotation of the image sensors about their respective central rotational axis as well as the rotation of the image sensors relative to each other about the central longitudinal axis of the shaft, as well as any radial and/or axial movements, are controlled independent of each other, yet synchronized with each other. This also makes it possible to keep the orientation of the individual image sensors constant, or respectively adjustable and constant, whereas the position relative to each other about the longitudinal axis of the endoscope shaft is variably adjusted.

In a preferred further development, a manually-operated or electrical drive is provided for rotating the sensor unit, image sensors, optical deflective elements and/or a section of the shaft which comprises the viewing window. A manually-operated drive comprises for example a control ring on the handle that is connected to the components to be rotated and moved by means of cables, rods or gear drives or other known mechanical measures. Piezoelectric motors, ultrasonic motors, miniature electric motors and the like are suitable electric drives.

For this purpose, a control apparatus is preferably provided in the stereo endoscope, or in the stereo endoscopy system beyond the one in the stereo endoscope, that controls the electric drives for rotating or respectively moving the individual components.

An orientation sensor is preferably provided by means of which an orientation of the sensor unit and/or image sensors can be specified within space, wherein in particular the regulation of the orientation and/or the spatial position of the sensor unit and/or image sensors is provided by means of signals from the orientation sensor. The signals from the orientation sensor are preferably used to keep the image sensors in a stable horizon position while regulating the rotation.

The stable horizon position corresponds, for example, to the direction of gravity or a direction that is desired and set by the operating surgeon and that is kept constant by means of the signals of the orientation sensor, even when the direction of view of the stereo endoscope changes. The preferably provided control apparatus can be operated by the operator and/or supplied with orientation data from an orientation sensor. A combination of these two designs enables the operator or surgeon to select a preferred orientation that can be maintained with the assistance of the orientation sensor and the control apparatus during surgery.

The object addressed by the invention is consequently also achieved by a stereo endoscopy system comprising the above-described stereo endoscope according to the invention as well as an image evaluating and reproducing apparatus, in particular a monitor and/or a computer system with a monitor that is/are designed to reproduce a stereoscopic video image. A stereo endoscopy system according to the invention also comprises equipment such as shutter glasses or glasses with polarized lenses, if applicable. Furthermore, the stereo endoscopy system comprises a control apparatus for setting desired recording and reproduction parameters, including in particular the horizon position.

All of the cited features, properties and advantages of the subject matter of the invention, i.e. the stereo endoscope according to the invention and stereo endoscopy system according to the invention, apply without restriction to all other subject matter of the invention.

The invention will be described below without restricting the general inventive idea using exemplary embodiments that refer to the drawings, and regarding any details according to the invention which are not explained further in the text reference is expressly made to the drawings. In the figures:

FIG. 1 shows schematic views of a stereo endoscope according to the invention,

FIG. 2 shows schematic views of another stereo endoscope according to the invention, FIG. 3 shows a schematic representation of another stereo endoscope according to the invention, and FIG. 4 shows two detailed representations of a stereo endoscope according to the invention from FIG. 3.

In the following figures, equivalent or similar elements or respectively corresponding parts are provided with the same reference numbers so that a corresponding re-introduction is omitted.

FIG. 1 schematically portrays a highly shortened stereo video endoscope 1 according to the invention having a rigid shaft 1a, on the distal tip of which an inclined viewing window 2 as well as a sensor unit with two image sensors 5, 5' are arranged.

The representation portrayed in FIG. 1 a) is from the side so that only one image sensor 5 is visible with one prism 3 and one lens assembly 4. The front surface of the prism 3 is arranged parallel and at a slight distance from the viewing window 2. Both have a slight inclination. The second combination consisting of the prism 3', lens assembly 4' and image sensor 5' is arranged hidden behind it.

Electrical cables 6 are also schematically portrayed which supply the image sensor 5 with power and send the obtained image data to an evaluation apparatus (not shown). The shaft 1a has an orientation sensor 9 which monitors the orientation of the shaft in space. The position of the orientation sensor 9 is located in the circumferential direction of the shaft 1a approximately where the inclined viewing window 2 is axially most withdrawn. The specific arrangement of the orientation sensor 9 is freely selectable. A dot-dashed central rotational axis 8 of the shaft 1a is also portrayed. Schematically portrayed at the proximal end are supply and data cables 7.

FIG. 1 b) shows the stereo video endoscope 1 in the same state as in FIG. 1 a), however from a different perspective corresponding to a direction of view from below in FIG. 1 a). From this perspective, the components of the prism 3, the lens assembly 4 and sensor 5 can be seen which are also depicted in FIG. 1 a), along with the prism 3', lens assembly 4' and sensor 5' as well as the associated electrical cable 6' which cannot be seen in FIG. 1 a). The image sensor 5 in FIGS. 1 a) and 1 b) is an image sensor that records an image for a left eye, whereas the image sensor 5' records an image for a right eye. Proceeding therefrom, the direction of view of the stereo video endoscope 1 points downward.

FIGS. 1 c) and 1 d) show a different situation in which the stereo video endoscope 1 looks sideways to the left wherein it is assumed that the image sensor 5 supplies image information for a left eye, whereas the image sensor 5' supplies image information for a right eye. In comparison to the situation shown in FIGS. 1 a) and 1 b), the viewing window 2 and the prisms 3, 3' are rotated 90° in FIGS. 1 c) and 1 d), whereas the groups consisting of the optical deflective elements 3, 3', the lens groups 4, 4' and image sensors 5, 5' are axially shifted relative to each other. The front surfaces of the prisms 3, 3' therefore remain parallel and at the same distance from the viewing window 2.

FIGS. 1 a) to 1 d) each show that the active surface for recording image information only takes up the central part of the viewing window 2. The unused surface is employed to illuminate the operative field by means of lighting elements (not shown). These can be fiberglass bundles that guide light from a lamp (not shown) to the distal tip of the shaft 1a, or for example LED luminaries.

FIG. 2 portrays an alternative version of a stereo video endoscope 11 according to the invention in and from various perspectives and directions of view. FIG. 2 a) portrays a stereo video endoscope 11 with a rigid shaft 11a, on the distal tip of which an inclined viewing window 12 and an individual prism 13 are arranged. To change a direction of view, at least the section of the shaft 11a is rotated that comprises the viewing window 12 and prism 13. The viewing window 12 can also be part of the prism 13. Following the prism are lens assemblies 4, 4' and image sensors 5, 5' with electrical cables 6 and 6' which are arranged in the same manner as shown in FIG. 1 a) to d).

FIG. 2 a) shows a situation in which the optical components are viewed from the side. Given that the image sensor 5 supplies image information for the left eye, the direction of view of the stereo video endoscope 11 is directed downward. The same situation is viewed from below in FIG. 2 b). In this case, both image sensors 5, 5' can be seen with corresponding components.

FIG. 2 c) shows an altered situation in which the stereo video endoscope 11 looks sideways to the left. FIGS. 2 c) and 2 d) reproduce the views from the side and from below. In the case of a stereo video endoscope 11 according to FIG. 2a) to d), an orientation sensor 9 is located close to the distal tip of the shaft 11a. The axis of symmetry or respectively longitudinal axis 8 of the stereo video endoscope 11 is also shown in FIGS. 2a) and 2b).

An endoscope with rod lenses can be designed analogous to FIGS. 2a-2d in which the rod lenses send the images to a proximal ocular and a connected camera head. In both cases, the unit consisting of the viewing window 12 and prism 13 can be part of an exterior shaft (not shown) that runs proximally up to the handle of the video endoscope or to the ocular, whereas the lens assemblies 4, 4' and the image recorder 5, 5', or respectively the rod lenses, are arranged in an inner shaft that is rotatably mounted within the outer shaft, and is nonrotatably connected to the handle of the endoscope or to the camera head. A rotary ring can be arranged on the proximal end of the exterior shaft so that the user can rotate the external shaft and hence the direction of view of the endoscope by rotating the rotary ring, whereas by holding tight the endoscope handle or the camera head, the position of the inner shaft and hence the position of the baseline can be kept constant.

FIG. 3 schematically portrays a third alternative of a stereo video endoscope 21 according to the invention that has a flexible shaft section 22 with a distal section having an optical sensor unit. The sensor unit arranged on the distal tip points in the 0° direction of the shaft 22. A lateral view is achieved by swinging the shaft. The sensor unit can be swung in different directions by means of the flexible section 22. Entry lenses 24, 24' for both image channels of the stereo video endoscope 21 are portrayed on the distal tip of the shaft 22, 23. Alternatively, the sensor unit can also be designed to look sideways.

The stereo video endoscope 21 has a handle 25 with a rotary ring 26 for adjusting the horizon position of the image sensors (not shown), and a flexible proximal section 27 which controls the bending of the flexible distal section 22. Rotating the shaft about the longitudinal axis at the site of the handle 25 causes the viewing angle to change and changes the horizon position of the two image sensors which are arranged behind the entry lenses 24, 24' in FIG. 3. In order to compensate for the shift of the horizon position, either a control of the sensor unit is provided in the distal section 23, or it is kept constant by holding tight the rotary ring 26.

The direction of view is adjusted by rotating the stereo video endoscope 21 about its central rotational axis or respectively longitudinal axis 8' both when the shaft is flexibly controllable in different directions, and when pivoting only occurs in a single plane. In the latter case, FIGS. 4 a) and 4 b) show that the sensor unit with the portrayed entry lenses 24, 24' can be rotated by turning the shaft or respectively the entire endoscope 21. The flexible shaft section 22 can only swing in a single direction 28 which is indicated by arrows. The horizon position which is also chosen to be horizontal in FIG. 4 a) is left by rotating the stereo video endoscope 21 about the central rotary axis 8'.

FIG. 4 b) shows that the sensor unit with the portrayed entry lenses 24, 24' is rotated back in the opposite direction, and the horizon position is assumed, wherein the swivel plane with the swivel direction 28 remains unchanged in comparison to FIG. 4 a). Thus, swinging in any desired direction is possible without changing the horizon position.

All of the cited features including those only found in the drawings, as well as individual features that are disclosed in combination with other features, are considered essential to the invention by themselves and in combination. Embodiments according to the invention can be realized by the individual features, or a combination of several features.

LIST OF REFERENCE NUMBERS

1 Stereo video endoscope
1a Shaft
2 Viewing window
3, 3' Prism
4, 4' Lens assembly
5, 5' Image sensor
6, 6' Electrical cable
7 Supply and data cable
8, 8' Central rotary axis
9 Orientation sensor
11 Stereo video endoscope
11a Shaft
12 Viewing window
13 Prism
21 Stereo video endoscope
22 Flexible distal shaft section
23 Distal section with optical sensor unit
24, 24' Entry lenses
25 Handle
26 Rotary ring
27 Proximal flexible section
28 Swivel direction
29 Front surface of the shaft

The invention claimed is:

1. A stereo endoscope comprising:
an elongated shaft; and
a sensor unit comprising two flat image sensors which are arranged symmetrically about a central rotational axis of the shaft,
wherein:
a lateral direction of view of the stereo endoscope which deviates from a central 0° direction of view can be variably adjusted and/or changed independent of an orientation of the image sensors relative to each other;
an optical deflective element corresponding to each of the two flat image sensors, wherein each of the optical deflective elements assigned to a corresponding one of the two flat image sensors can be rotated relative to the corresponding one of the two flat image sensors about a rotary axis;
each of the two flat image sensors together with the corresponding optical deflective element is movable in an axial direction of the shaft; and
the two flat image sensors are movable axially in opposite directions relative to each other in the axial direction of the shaft.

2. The stereo endoscope according to claim 1, wherein the sensor unit is arranged on one of a distal tip of the shaft or in a proximally arranged camera head.

3. The stereo endoscope according to claim 1, wherein the elongated shaft is configured as a rigid shaft, the distal end of which has a viewing window which is inclined relative to the longitudinal axis of the shaft and which is connected to at least one optical deflective element within the interior of the shaft, wherein for adjusting or changing the lateral direction of view, at least one distal section of the shaft with the viewing window and the at least one optical deflective element is rotated about an axis that is aligned parallel to the longitudinal axis of the shaft.

4. The stereo endoscope according to claim 1, wherein the axial movement of the image sensors and the optical deflective elements assigned to them are coupled to a rotary movement of the shaft for changing a direction of view so that the distances of the optical deflective elements to the viewing window remain the same.

5. The stereo endoscope according to claim 1, wherein a radial distance between the image sensors is changeable with the optical deflective elements assigned to them.

6. The stereo endoscope according to claim 1, wherein an orientation sensor is provided such that an orientation of one or more of the sensor unit and the image sensors in space can be determined based on signals of the orientation sensor.

7. The stereo endoscope according to claim 3, wherein at least one of the optical deflective elements comprise a prism.

8. The stereo endoscope according to claim 1, wherein the rotary axis runs through the midpoint of the image sensor.

9. The stereo endoscope according to claim 5, wherein a change of the optical distance is coupled to the axial movement of the image sensor so that a spacing of the image sensors provided perpendicular to the direction of view remains constant.

10. The stereo endoscope according to claim 1, wherein each of the optical deflective elements comprise a prism.

\* \* \* \* \*